Figure 1:
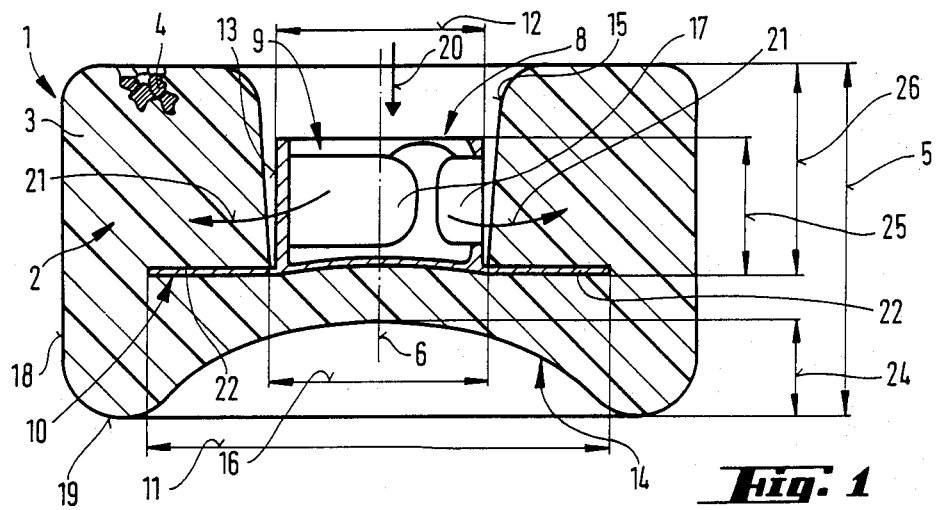

United States Patent [19]

Pickhard et al.

[11] Patent Number: 4,883,071
[45] Date of Patent: Nov. 28, 1989

[54] INTRAVAGINAL DEVICE

[76] Inventors: Ewald Pickhard, Redtenbachergasse 15, A-1160 Vienna; Wolfgang Knogler, Görgengasse 27, A-1190 Vienna, both of Austria

[21] Appl. No.: 294,933

[22] Filed: Jan. 4, 1989

Related U.S. Application Data

[63] Continuation of Ser. No. 908,704, Aug. 28, 1986, abandoned.

[30] Foreign Application Priority Data

Nov. 15, 1984 [AT] Austria ................................. 3622/84
Jul. 2, 1985 [AT] Austria ................................. 1956/85

[51] Int. Cl.⁴ .............................................. A61F 5/46
[52] U.S. Cl. ...................................... 128/837; 128/834
[58] Field of Search ............... 128/830, 832, 834, 837, 128/838–841; 604/55, 93, 891, 892

[56] References Cited

U.S. PATENT DOCUMENTS

| | | | |
|---|---|---|---|
| 3,042,029 | 7/1962 | Johansson | 128/127 |
| 4,261,352 | 4/1981 | Sedlacek | 128/127 |
| 4,300,544 | 11/1981 | Rudel | 128/127 |
| 4,326,510 | 4/1982 | Buckles | 128/127 |
| 4,360,013 | 11/1982 | Barrows | 128/832 |
| 4,564,362 | 1/1986 | Burnhill | 604/286 |

Primary Examiner—Robert A. Hafer
Assistant Examiner—Kevin G. Rooney
Attorney, Agent, or Firm—Collard, Roe & Galgano

[57] ABSTRACT

The intravaginal device is comprised of a plastic body (2) wherein a drug is contained. Said device may be particularly used for contraception. A support (8) is arranged into the body which is formed of a preferably cylindrical block of plastic foam. It has an opening (15) parallel and preferably centered to the axis of the cylinder forming the block. This opening may preferably be a blind hole. The support is arranged in the opening. Said support is connected with the body by means of an element embedded in the foam. The invention also discloses a method for handling said device as well as a handling device for implementing the method for introducing, respectively removing said device.

15 Claims, 1 Drawing Sheet

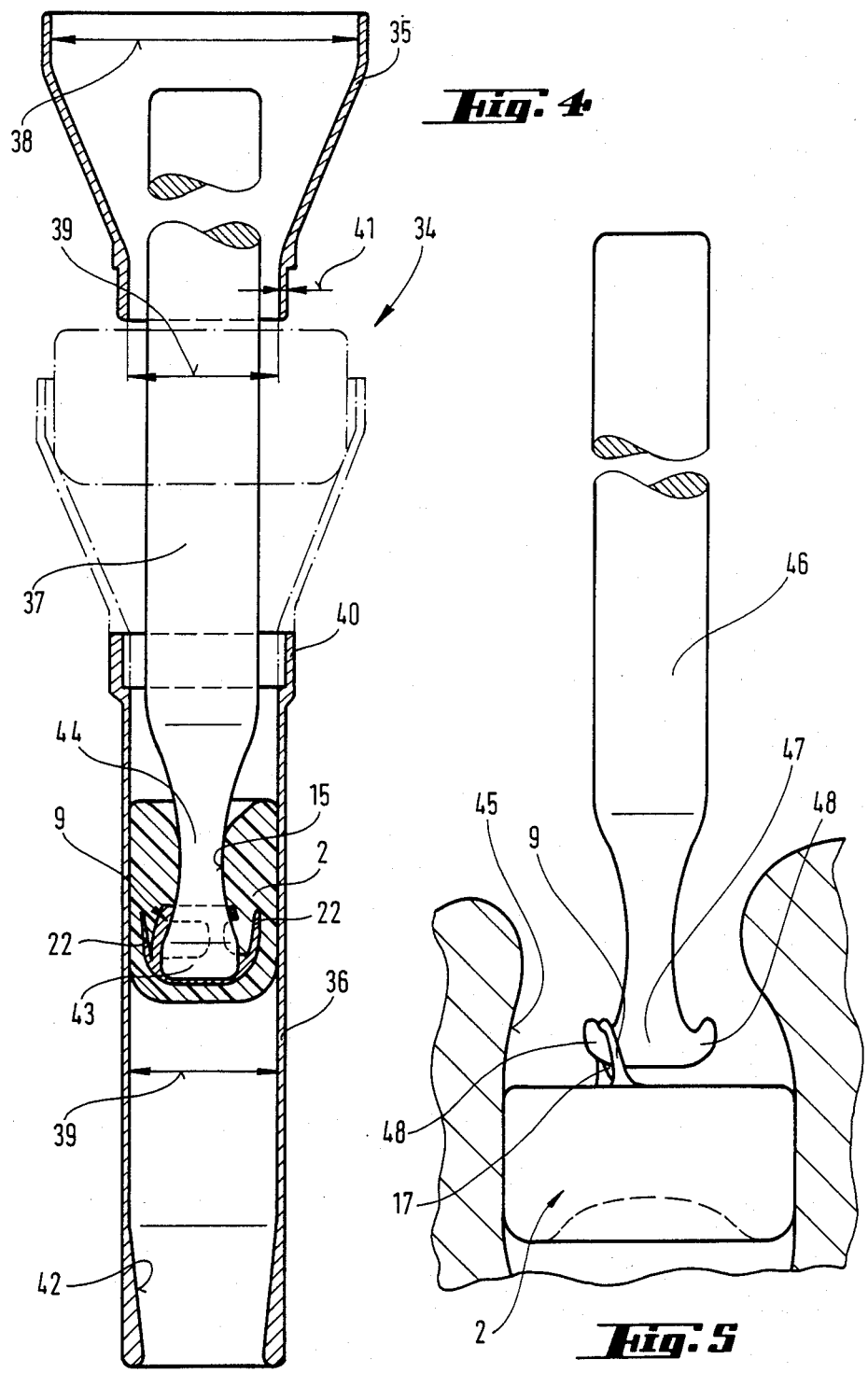

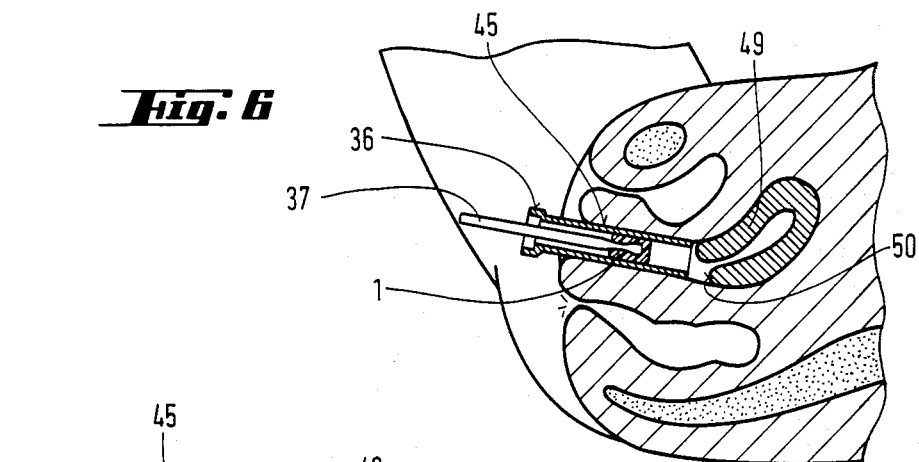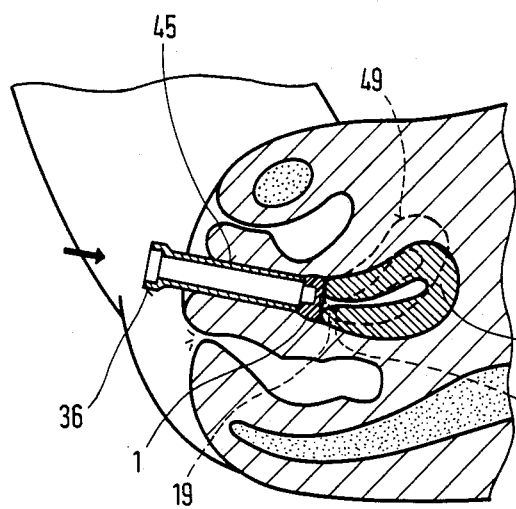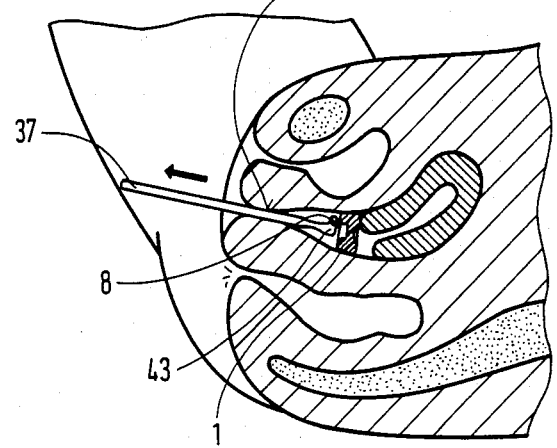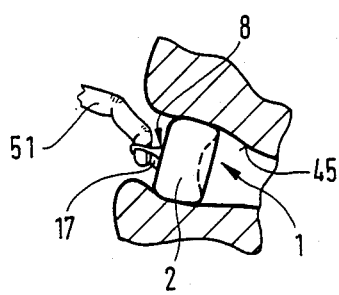

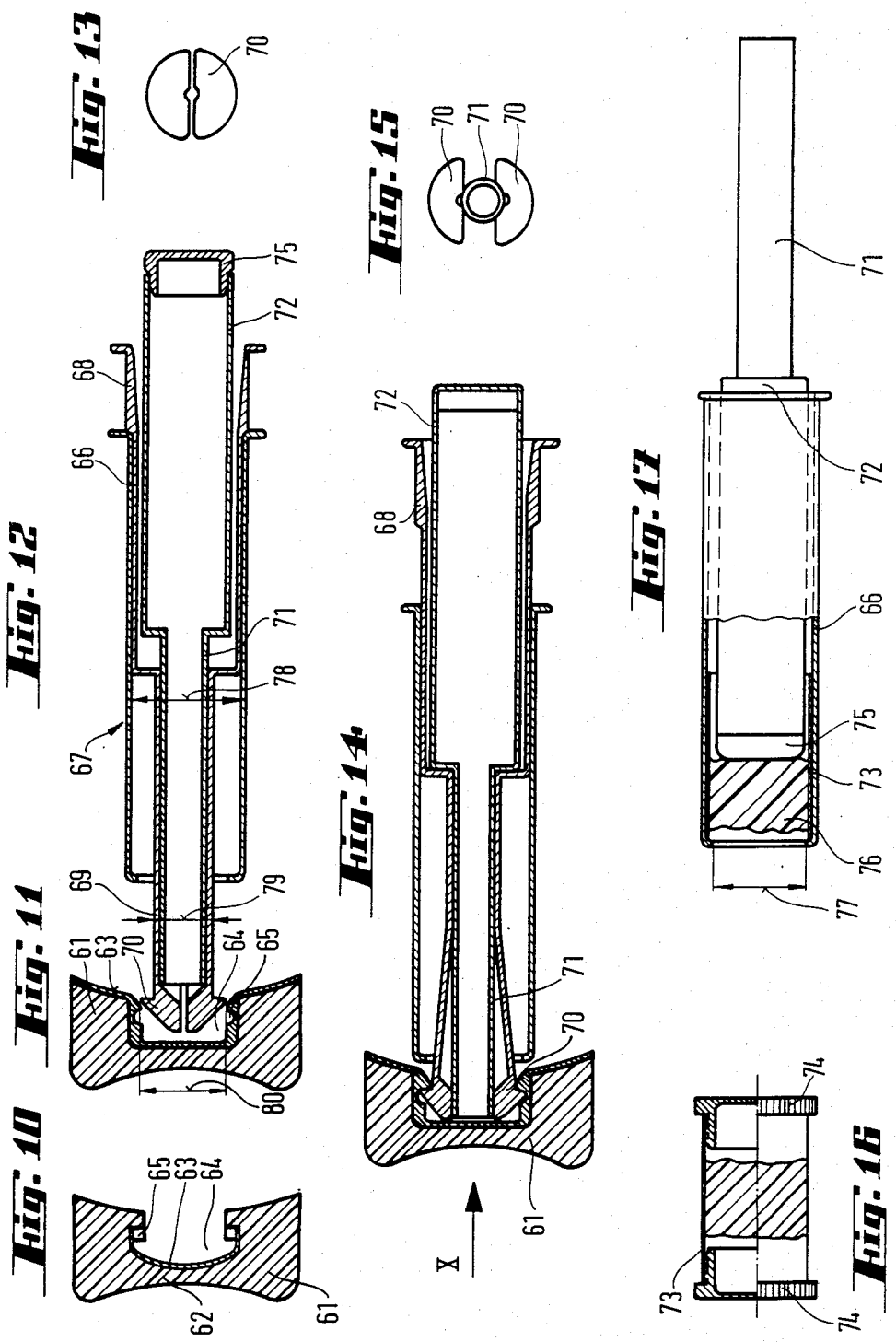

INTRAVAGINAL DEVICE

This is a continuation of our U.S. patent application Ser. No. 908,704, filed Aug. 28, 1986, now abandoned.

The invention relates to an intravaginally positionable and in particular contraceptive device comprising an elastic carrying element consisting of synthetic resin material and absorbing a medication, which is provided with an entraining member.

Contraceptive sponges of this nature form part of the oldest methods of preventing conception, and sponges which were impregnated with vinegar or oil became known in antiquity. In the case of recently proposed systems of the kind defined in the foregoing, the vinegar or oil was replaced by chemical spermicides, whilst retaining the basic principle of a sponge which is impregnated with spermicide and is intended to act contraceptively in this manner. The unwieldy and unpleasant handling of the small sponge for its positioning within the intravaginal section is disadvantageous in these systems. Since the spongelet has to be pushed into its position, it loses a large part of its absorbed liquid by mechanical compression and it was also found that the damp synthetic resin material feels unpleasant to the touch.

A known device of this kind, U.S. Pat. No. 4,219,016, comprises a cap formed from several synthetic resin material sheets, as a carrying element. This cap has an approximately circular cross-section and is spatially curved in the direction at right angles thereto. An annularly encircling reinforcing ring is commonly situated in the terminal circular portion, which restores the terminal portion to the required peripheral shape after compression or expansion. A medication or spermicide is placed in each case between two sheets formed from different synthetic resin materials in particular, whereby the semen is intended to be killed upon utilising this device as a contraceptive means. The unstable structure of these caps attributable to the utilisation of thin sheet-like elastic materials renders it difficult to insert such carrying elements into the vagina as well as to extract the same.

Other known devices of this kind comprise a cylindrical carrying member of elastic plastics material or sponge, which are coated or impregnated with a medication such as a spermicide in particular. The height of these cylindrical carrying members is smaller than their diameter. These carrying members are inserted and positioned manually in the vagina by the female user. Because of the different positions of the uterus at the extremity of the vagina, it is possible to obtain an unequivocal positioning with difficulty only, or rather, the smooth end sides of the carrying member could cause shifting during sexual intercourse and thus a loss of effectiveness of the device.

According to another known device, according to DE-PS No. 822,877, a cylindrical carrying member is equally provided which has a smaller height than a diameter of the same. One of the end sides of the cylindrical carrying member is concavely curved, this curvature being substantially matched to the median outline of the neck of the womb. The oppositely situated end side equally has a concave depression, over which extends a rubber band. The carrying member comprises two parts which are bonded together, preferably under inclusion of a damp-proof foil. The carrying member or the separate parts of the carrying member, is or are formed by natural or synthetic sponges. The carrying member is charged with a medication prior to introduction into the vagina. What is unfavourable in this connection is the composite structure of the carrying member and the risk established by the same, that the two parts of the carrying member may separate from each other, and that this may lead to trouble. The extraction of such devices is intended to be facilitated by means of a strap or tie situated above the opening a the end facing towads the neck of the womb.

The object of the present invention consists in devising an intravaginally positionable and in particular contraceptive device which assures safe positioning within the vagina, especially in the area of the neck of the womb, and which may easily be inserted and extracted.

In the case of a device of the kind described in the foregoing, the problem of the invention is resolved in that the carrying member is formed by a substantially cylindrical block of a synthetic resin foam material which is provided with an aperture extending concentrically with respect to the axis of the cylinder, and defining a blind hole, in which an entraining element is situated and joined to the carrying member during foaming of the material of the cylindrical block. The unexpected advantage of this solution consists in that thanks to the appropriately shaped carrying member, a satisfactory fit of the same is obtained within the vagina, in particular in the area of the cervix, and that the carrying member remains securely in the required position during sexual intercourse. Furthermore, the opening extending in the direction of insertion acts as a semen collector. The medication contained in the carrying member can act intensively on the semen collected in the opening, thereby killing off a large porportion of the spermatozoons immediately and reliably. The residual spermatozoons are killed off reliably upon passing through the carrying member by the medication present within the same, so that satisfactory protection is available against an undesirable conception during application as a contraceptive means. Another advantage consists in that no unpleasant side-effects are experienced by the wearer of a device of this kind thanks to the elastic structure of the carrying member, whilst nevertheless assuring resiliency by an appropriate configuration of the internally situated entraining element.

Provision is made according to another feature of the invention for the entraining element to have a surface facing towards the carrying member integrally joined to this carrying member in the area of the opening during the foaming process. Thanks to this integration of the entraining element in the foamed carrying member, the entraining element remains within said opening and is not detected as a nuisance outside the same, in particular within the vagina. A firm retention of the entraining element within the carrying member is obtained moreover, so that the entraining element is prevented from being torn out even if greater forces are exerted during the withdrawal of the device according to the invention.

It is advantageous furthermore for the carrying member to be formed from an open-pored synthetic resin material foam, in particular a soft polyurethane foam, which preferably also has open cells in the area of the surface, since this allows of traversal by humidity and body fluid, for example for dissolving or activating the medication contained in the carrying member, a penetration of the spermatozoons into the carrying member as well as an egress of the medication out of the carrying member even in the area of the surface of the carrying member being rendered possible by the open cells. Thanks to the constant pH value of the open-pored plastics material foam, the latter displays a satisfactory level of compatibility with the body.

It is also possible moreover for the carrying member to be formed in one piece and for the cells situated at the other side from the opening to be closed, in particular by appropriate temperature control during the expanding operation. It is advantageous in the case of this solution that a compact carrying member is produced, which remains in one piece even under the action of body fluids and the like and primarily also during withdrawal from the vagina, and that an uncomplicated extraction is assured thereby. If the carrying member moreover has wholly closed cells at the end side facing away from the opening—for example by forming a skin on the surface of the expanded carrying member by appropriate temperature control during the expanding operation—a traversal by spermatozoons towards the uterus is prevented completely.

Provision is made according to another modified embodiment of the invention for an end face of the carrying member facing away from the opening to be concavely formed and for a transition between this concave end face and outer surface of the carrying member to be rounded off and in particular to form an encircling peripheral rim, thereby assuring satisfactory adaptation to the cervix of the uterus. An unobjectionable insertion is rendered even in the case of different positions of the uterus with respect to the vagina. The uterus is more liable to assume a position parallel to the vagina, primarily upon inserting and pushing home the carrying member. Following the insertion, when it returns to its original position, it is moved over the rim enlargement by the cervix and held in the corresponding correct position.

Provision is made according to another form of embodiment for a depth of the curvature of the concave end face to be smaller than a height of the carrying member minus an overall height of the cylinder forming the entraining element. It is accomplished thereby that an uninterrupted elastic synthetic resin material foam is also present in the area of the concave end face, thereby securing a reliable anchoring of the entraining element formed by a cylinder and pleasant wearing properties. The synthetic resin material foam is thermally insulating and feels "warm" to the touch, so that no unpleasant temperature reaction is detectable even during insertion of the carrying member.

According to another modified embodiment, the entraining element consists of a synthetic resin material cylinder, openings being provided in a cylinder jacket of the cylinder and the cylinder being open at one end and closed by an end wall at the other end and anchoring elements are provided in the area of this end wall at least, for example a ring arranged to project with respect to the cylinder jacket at a distance from the end wall or in the area of the end wall for anchoring purposes. The openings in the cylinder surface form gripping means which may be grasped by a finger or into which a rod may be hooked for withdrawal, to allow of uncomplicated and safe extraction of the device. If the cylinder is formed by a damp-proof material, spermatozoons may be prevented from passing into the uterus without obstruction through the comparatively thin portion in the direction of the axis of the cylinder, by the fact that the other end side is sealed off. On the contrary, the semen received is deflected sideways into the surrounding portion of the carrying member where it undergoes intensive contact with the spermicide contained in the carrying member and is killed off in this manner. A secure and tear-proof fit of the entraining element in the carrying member is assured by the anchoring elements situated on the cylinder. Thanks to the incorporation of a continuous end wall in the base portion of the opening in the form of a blind hole, a finger or the push rod utilised for insertion may bear on the same, thereby preventing tearing or puncturing of the thin-walled portion between the end wall of the cylinder and the concave end face of the carrying member oppositely situated thereto during the insertion, so that a reliable operation of the carrying member is assured.

It is also possible moreover for the end wall of the entraining element to have a diameter which is greater than an outer diameter of the cylinder, but smaller than the diameter of the carrying member. This has the advantage that the spermatozoons passing through in the direction of the axis of the cylinder are deflected reliably in transverse direction through the carrying member and come into intimate contact with the spermicide contained in the carrying member.

It is also advantageous if the entraining element is formed from an elastomeric synthetic resin material, in particular an elastic silicone rubber and/or soft PVC and/or "pharma"-rubber and/or thermoplastic rubber, becuase a resilient action of the entraining element and a satisfactory compability for insertion into the body, are obtained thereby. Furthermore, synthetic resin materials of this nature are tough and elastic and have a high tearing strength whilst being damp-proof at the same time, so that the two principal functions of the entraining element—namely reliably insertion and withdrawal of the device in accordance with the invention—are secured.

It is also possible however that an internal diameter of the blind hole present in the carrying member substantially corresponds to an internal diameter of the entraining element produced in the form of a cylinder, and that a blind hole depth substantially corresponds to an overall height of the cylinder forming the entraining element, thereby facilitating insertion without impeding sexual intercourse.

Provision may also be made for a height of the carrying member to amount to a part only of a diameter of the same, and to be greater than an overall height of the cylinder acting as an entraining element, thereby securing satisfactory elasticity in radial direction.

It is also advantageous if a diameter of the blind hole and/or of the cylinder forming the entraining element is smaller than a half of the diameter of the carrying member, since an adequate volume of the carrying member is made available thereby for reception of the spermicide.

Provision is made according to another modified embodiment for the entraining element to be formed by a net of an elastomeric synthetic resin material or the like and for this net to be integrated by co-expansion in the carrying member at approximately half the height of the opening. This secures the advantage that the carrying member is reinforced by the imbedded net element, the withdrawal being easily possible however despite this, by catching a mesh opening.

It is also advantageous if a diameter of the opening and/or the inner diameter of the cylinder forming the entraining element corresponds approximately to a mean diameter of a human finger and that the openings in the cylinder surface of the cylinder acting as an entraining element and/or the mesh size of the net forming the entraining element substantially correspond to the average diameter of a human finger, thereby also facilitating the insertion of the device with a finger and above all however the withdrawal of the device by means of a finger.

It is also possible however that an end face of the carrying member formed from porous synthetic resin material and oppositely situated to a concave end face may be fixedly joined and in particular bonded to the carrying member—at least at the periphery—via an element of elastomeric material produced in the form of a foil, film or panel, thereby even complementarily impeding the traversal by spermatozoons.

It is also possible however, that the element joined to the carrying member consists of elastic silicone rubber and/or soft PVC and/or pharma-rubber and is indissolubly joined to the carrying member consisting of soft expanded polyurethane by means of a pharmacologically safe adhesive, thereby reliably preventing substances harmful to health from being formed by evaporation of solvents or the like.

It is also advantageous if the bonded area between the carrying member and said element is concavely shaped, thereby securing a better adhesion between these two parts and an improved stability of the device.

Provision is made according to a modified embodiment that the porous carrying member comprises metal filaments of copper or silver, thereby intensifying the spermicidal action of the device.

It is also advantageous however if the edges of the element covering the end face are bent over inwards through 180° and are glued to the end face of the carrying member. A structure is formed in this manner in which the bonded areas and thus a theoretically possible hardening are restricted to the circumference of the device or sponge, whereas the central part of the substantially hermetic foil rests on the carrying member in the manner of a diaphragm. The removal of a device of this kind or of a small sponge of this kind could be example be performed under application of a negative pressure, during which action this diaphragm could then be drawn into an appropriate suction tube.

Furthermore, it is also possible however for the carrying member to have a recess or depression or opening co-axial with the axis of the cylinder of the carrying member in its end face joined to the covering element and for the covering element to be bonded to the carrying member throughout its end face, thereby facilitating the positioning and withdrawal of the small sponge.

In this connection, it is advantageous if the recess of opening has at least one groove extending in peripheral direction, which is delimited by inwardly projecting rims and/or produced to C-shape in axial cross-section, thereby simplifying an engagement of a gripper for withdrawal of the device.

Figure 2:
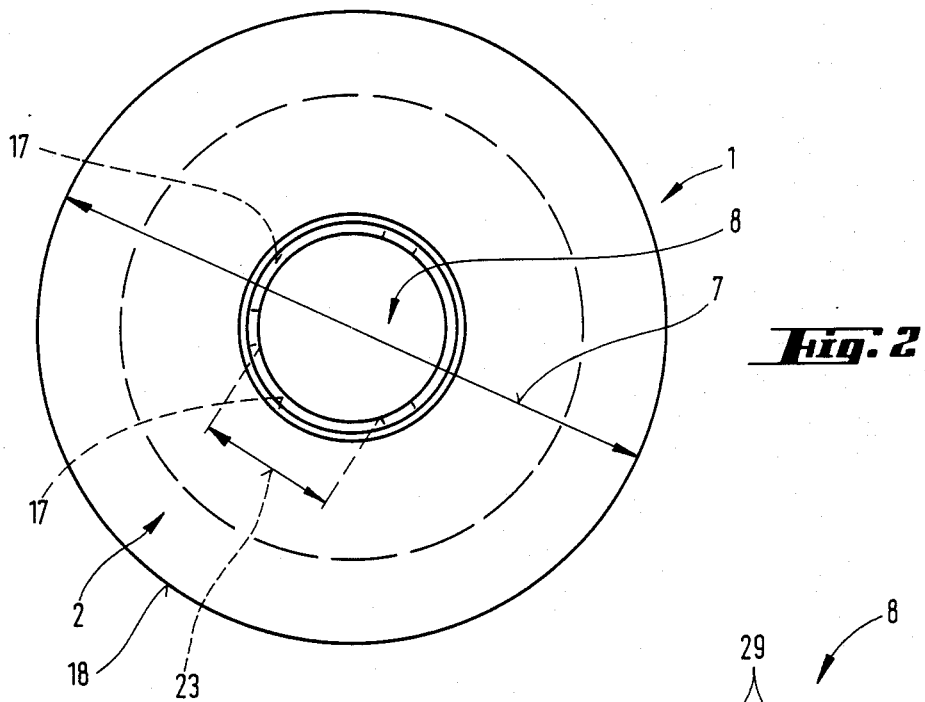
Figure 3:
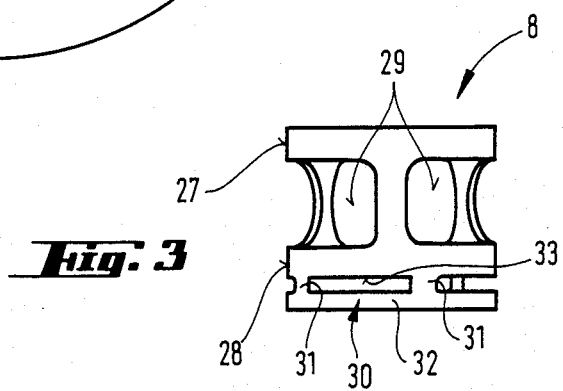

For a clearer grasp of the invention, the latter is described in particular in the following with reference to the embodiments illustrated in the drawings. In these:

FIG. 1 shows a device according to the invention in sideview, with the carrying member and entraining element cross-sectioned, FIG. 2 shows a plan view of the device according to FIG. 1, and FIG. 3 shows a modified embodiment of an entraining element in sideview.

An intravaginally positionable device 1 is illustrated in FIGS. 1 and 2. This device 1 comprises a carrying member 2 constituted by a cylindrical block of synthetic resin foam material 3, e.g. an expanded polyurethane. This material has a large proportion of open pores, as denoted diagrammatically in the sectioned area. As denoted by hatching, these open cells are charged with a medication 4 which may be injected into the finished material.

As most clearly apparent from FIG. 2, the carrying member 2 has a circular cross-section. A height 5 parallel to a cylinder axis 6 of the carrying member 2 is smaller than an outer diameter 7 of the carrying member, thereby securing satisfactory elasticity in radial direction.

An entraining element 8 is integrated in the carrying member during the foaming operation. In the present embodiment, the entraining element 8 is formed by a cylinder 9 which is closed off at one of its two ends by an end wall 10. This end wall 10 has a flange diameter 11 which is greater than an external diameter 12 of the cylinder 9. The end wall 10 has a flange portion projecting beyond diameter 12, i.e. cylinder surface 13, with which it is held in the carrying member 2. As apparent, this end wall 10 closed an opening 15 at an end directed towards end face 14 to form a blind hole. This opening 15 extending concentrically about cylinder axis 6 is conically formed in the present case and in the area of the end wall 10 of the entraining element 8 has a diameter 16 which is greater than the outer diameter 12 of the cylinder 9. The cylinder surface 13 thus stands wholly exposed within the opening 15. Since openings 17 are provided in the cylinder surface 13 moreover, this cylinder surface 13 forms several peripherally contiguous loops or catches into which may be hooked an extractor element or a finger to withdraw the carrying member 2 from the vagina.

It is evidently also possible however to form the opening 15 with a circular cross-section and to select the diameter 16 so that it corresponds substantially to the outer diameter 12 of the cylinder 9.

The end face 14 of the carrying member 2 is concavely formed, the transition between this concave end face and outer surface 18 being rounded off considerably to form an annular rim 19. The area enclosed by the rim is adapted in shape to the average outline of the cervix, that is to say to the womb entrance, so that a satisfactory isolation of the uterus is the result. This has the advantage that if the carrying member 2 is charged with medications serving the purpose of treating the vagina or the womb, these may be deposited in the corresponding sections and that an areal contact and a satisfactory isolation of the cervix are then available when the device 1 is utilised as a contraceptive means.

In the case in which the device 1 is utilised as a contraceptive means, it is advantageous for the end wall 10 to have a diameter 11 corresponding to that of the area surrounded by annular rim 19 and to be formed from a liquid impermeable synthetic resin material, for example an elastic silicone rubber and/or soft PVC and/or a "pharma' rubber and/or thermoplastic rubber, for example such as "Kraton". The spermatozoons penetrating parallel to the cylinder axis 6 in the direction of arrow 20 during sexual intercourse are deflected into the carrying member 2 by this impermeable end wall 10, as shown diagrammatically by arrows 21, in which they are placed in intimate contact during traversal of the open cells with the medication or spermicide 4 contained therein. The spermatozoons are killed off thereby. Furthermore, the transit passage cross-section between the outer surface 18 of the carrying member 2 and the end wall 10 is so restricted that a rapid traversal of spermatozoons or deleterious substances through the carrying member is practically precluded. Above all, a rapid traversal of spermatozoons or deleterious substances through the thin-walled section between the end wall 10 and the end face 14 is prevented in the direction of the uterus, and this end wall 10 also eliminates tearing of the expanded synthetic resin material during insertion or during sexual intercourse.

Nevertheless and advantageously, no sections projecting or protruding beyond the carrying member 2 are present as entraining elements for extraction or insertion of the carrying member 2 into the vagina.

The flange of the end wall 10 projecting beyond the external diameter 12 forms anchoring element 22 for seucre retention of the entraining element 8 in material 3 of the carrying member 2.

As more clearly apparent diagrammatically from FIG. 2, the openings 17 have a diameter 23 which corresponds substantially to a diameter of a human finger, so that cylinder surface 13 may easily be grasped and utilised for safe withdrawal of the carrying member 2 from the vagina.

The appropriate shaping of the end face 14 in adaptation to the outline of the cervix at the entry to the uterus furthermore assures that the carrying member is prevented from slipping off the cervix and from failing to provide continued protection upon resetting the womb into the natural position by withdrawal of the finger or of the guiding tube from the vagina after being positioned at the cervix, at different positions of the uterus and in particular after deflection of the womb into an inverted position, as remains to be described in the following with reference to the diagrammatical illustrations in FIGS. 6 to 9.

To prevent penetration of harmful substances into the uterus, it is also possible to form the end face 14 with closed pores, to which end the polyurethane material foam may be formed with a hermetic skin during the expanding action by appropriate temperature control within the mould, during which this section of the mould is kept cooler than the other sections of the mould, so that a hermetic end face 14 is obtained.

It is advantageous furthermore if the diameter 12 of the cylinder 9 is smaller than half the diameter 7 of the carrying member 2. Sufficient volume of open-pored material foam is thus retained for reception of an appropriate quantity of a medication.

A depth 24 of the concave curvature of the end face 14 is smaller than the height 5 of the carrying member 2 minus an overall height 25 of the cylinder 9 forming the entraining element 8.

In the present embodiment, a blind hole dpeth 26 of the opening 15 is greater than the overall height 25 of the entraining element 8. It is however obviously also possible within the scope of the invention for the blind hole depth 26 and the height 25 to be approximately identical.

A modified embodiment of the entraining element 8 is illustrated in FIG. 3. This entraining element 8 comprises a cylinder 27 whereof the cylinder surface 28 defines openings 29 which correspond to the openings 17 of the entraining element 8 in FIGS. 1 and 2. A ring 32 of synthetic resin material spaced apart by webs 31 is provided as an anchoring element 30. Thanks to this ring 32 spaced apart from an end wall 33 of the cylinder 27, a retention of the entraining element 8 in the synthetic resin.

Different materials may equally be utilised for the entraining elements, the "Kraton" product, being a thermoplastic rubber, having proved to be particularly satisfacory. Soft polyurethane foams having a very low spatial weight and an open-celled structure are primarily appropriate for the production of the carrying member 2.

It is evidently also possible to produce the external shape of the device 1 in optional form, particularly in the area of the end face or else in the area of the peripheral surface of the cylinder jacket or of the end side oppositely situated to the end face. Furthermore, the cross-sectional shape need not moreover be circular in the direction of insertion but may also be ellipsoidal or polygonal or the like under particular circumstances.

We claim:

1. An intravaginally positionable device consisting essentially of an elastic carrying member of a synthetic resin foam having a medication incorporated therein, the carrying member comprising a substantially cylindrical block of the synthetic resin foam and the cylindrical block having a cylindrical wall defining a blind hole extending concentrically about the axis of the cylindrical block to an edge thereof, and an entraining element anchored in the carrying member during foaming of the synthetic resin foam to form the elastic carrying member, the entraining element not extending beyond the edge and having a cylindrical surface extending upwardly adjacent the cylindrical wall, and the cylindrical surface of the entraining element defining openings capable of being engaged by a member for insertion or extraction of the device into and from the vagina.

2. The intravaginally positionable device of claim 1, wherein the synthetic resin foam is an open-celled foam.

3. The intravaginally positionable device of claim 2, wherein the open-celled synthetic resin foam is a soft polyurethane foam.

4. The intravaginally positionable device of claim 2, wherein the carrying member comprises a synthetic resin foam portion extending below the blind hole and integrally formed with the cylindrical block, the foam of said portion at least at the surface thereof being closed-celled.

5. The intravaginally positionable device of claim 4, wherein the portion of the carrying member extending below the blind hole has a concave end face extending concentrically about the cylindrical block axis and facing in a direction opposite to that of the blind hole, and a rounded-off rim extending concentrically about the cylindrical block axis surrounds the concave end face.

6. The intravaginally positionable device of claim 1, wherein the entraining element surface is radially spaced from the blind hole wall.

7. The intravaginally positionable device of claim 6, wherein the carrying member comprises a synthetic resin foam portion extending below the blind hole and integrally formed with the cylindrical block, the portion of the carrying member extending below the blind hole having a concave end face extending concentrically about the cylindrical block axis and facing in a direction opposite to that of the blind hole, and the concave end face having a depth that is smaller than the total axial length of the carrying member minus the axis length of the entraining element.

8. The intravaginally positionable device of claim 7, wherein the entraining element is a cylindrical member of synthetic resin defining said openings therein, and the cylindrical entraining element member comprises anchoring means at one end thereof for anchoring the entraining element to the carrying member during the foaming of the synthetic resin.

9. The intravaginally positionable device of claim 7, wherein the openings in the cylindrical surface of the entraining element member have a diameter corresponding approximately to the average diameter of a human finger.

10. The intravaginally positionable device of claim 8, wherein the anchoring means is an annular flange portion radially projecting from the one end of the cylindrical entraining element member and anchored in th synthetic resin foam between the cylindrical block and said portion.

11. The intravaginally positionable device of claim 8, wherein the anchoring means is a ring integrally connected to, and axially spaced from, the one end of the entraining element member and anchored in the synthetic resin foam.

12. The intravaginally positionable device of claim 8, wherein the cylindrical entraining element member is open at one end and has a fluid-impermeable end wall closing the opposite end adjacent said portion.

13. The intravaginally positionable device of claim 12, wherein the end wall has a diameter greater than the outer diameter of the cylindrical entraining element member but smaller than the outer diameter of the carrying member.

14. The intravaginally positionable device of claim 1, wherein the axial length of the carrying member is smaller than the outer diameter thereof and the axial length of the blind hole exceeds that of the entraining element.

15. The intravaginally positionable device of claim 1, wherein the diameter of the blind hole is smaller than half of the outer diameter of the carrying member.

* * * * *